(12) United States Patent
Zhu et al.

(10) Patent No.: US 11,883,819 B2
(45) Date of Patent: Jan. 30, 2024

(54) REFRIGERATOR

(71) Applicants: QINGDAO HAIER REFRIGERATOR CO., LTD., Shandong (CN); HAIER SMART HOME CO., LTD., Shandong (CN)

(72) Inventors: Xiaobing Zhu, Qingdao (CN); Bin Fei, Qingdao (CN); Yongsheng Sun, Qingdao (CN); Haoquan Liu, Qingdao (CN)

(73) Assignees: QINGDAO HAIER REFRIGERATOR CO., LTD., Shandong (CN); HAIER SMART HOME CO., LTD., Shandong (CN)

( * ) Notice: Subject to any disclaimer, the term of this patent is extended or adjusted under 35 U.S.C. 154(b) by 0 days.

(21) Appl. No.: 18/246,486

(22) PCT Filed: Sep. 10, 2021

(86) PCT No.: PCT/CN2021/117714
§ 371 (c)(1),
(2) Date: Mar. 23, 2023

(87) PCT Pub. No.: WO2022/062919
PCT Pub. Date: Mar. 31, 2022

(65) Prior Publication Data
US 2023/0271184 A1 Aug. 31, 2023

(30) Foreign Application Priority Data
Sep. 27, 2020 (CN) .......................... 202011029619.7

(51) Int. Cl.
*B01L 3/00* (2006.01)
*F25D 23/02* (2006.01)

(52) U.S. Cl.
CPC ...... *B01L 3/502715* (2013.01); *F25D 23/028* (2013.01); *B01L 2200/027* (2013.01);
(Continued)

(58) Field of Classification Search
CPC ......... B01L 3/502715; B01L 2200/027; B01L 2200/04; B01L 2200/0689;
(Continued)

(56) References Cited

U.S. PATENT DOCUMENTS

| | | | | |
|---|---|---|---|---|
| 5,230,866 A | * | 7/1993 | Shartle | B01L 3/502723 422/68.1 |
| 5,498,392 A | * | 3/1996 | Wilding | B01J 19/0093 422/50 |

FOREIGN PATENT DOCUMENTS

| | | |
|---|---|---|
| CN | 103196887 A | 7/2013 |
| CN | 204165319 U | 2/2015 |

(Continued)

OTHER PUBLICATIONS

International Search Report and Written Opinion for PCT/CN2021/117714 (ISA/CN) dated Dec. 8, 2021 w/English translation (8 pages).
Written Opinion of the International Searching Authority for PCT/CN2021/117714 (ISA/CN) dated Dec. 8, 2021 (3 pages).

*Primary Examiner* — Christine T Mui
(74) *Attorney, Agent, or Firm* — ALSTON & BIRD LLP (57) ABSTRACT

A refrigerator, comprising a microfluidic testing system used for qualitatively or quantitatively testing a preset test parameter of a sample liquid. The microfluidic testing system comprises: a microfluidic biochip which is provided with a sample inlet, a communication port and a testing pool formed inside the microfluidic biochip, wherein the sample inlet, the testing pool and the communication port are in sequential communication by means of a micro-channel; a chip mounting mechanism used for mounting the microflu- (Continued)

idic biochip; a sample liquid driving device in hermetic communication with the communication port, so as to promote the sample liquid in contact with the sample inlet to flow into the micro-channel and flow to the testing pool via the micro-channel; and a testing mechanism which is used for testing the testing pool to obtain the preset test parameter of the sample liquid.

11 Claims, 8 Drawing Sheets

(52) U.S. Cl.
CPC ............... *B01L 2200/04* (2013.01); *B01L 2200/0689* (2013.01); *B01L 2300/0609* (2013.01); *B01L 2300/0819* (2013.01)

(58) Field of Classification Search
CPC ..... B01L 2300/0609; B01L 2300/0819; F25D 23/028
USPC .................................................. 422/502, 500
See application file for complete search history.

(56) References Cited

FOREIGN PATENT DOCUMENTS

| CN | 109655421 A | 4/2019 |
| CN | 214039111 U | 8/2021 |
| KR | 20120011458 A | 2/2012 |

\* cited by examiner

REFRIGERATOR

CROSS-REFERENCE TO RELATED APPLICATIONS

The present application is a national phase entry of International Application No. PCT/CN2021/117714, filed Sep. 10, 2021, which claims priority to Chinese Application No. 202011029619.7, filed Sep. 27, 2020, which are each incorporated herein by reference in its entirety.

FIELD OF THE INVENTION

The present invention relates to refrigerating and freezing technologies, and particularly to a refrigerator.

BACKGROUND OF THE INVENTION

With the improvement of the living standard of people, pesticide residues, viruses, nutritional elements or other aspects of some edible food materials are usually required to be tested in daily life, so as to qualitatively or quantitatively obtain the conditions of the food materials. For example, due to the pesticide abuse problem, fruits, vegetables and agricultural and sideline products purchased daily by people may have the problem of excessive pesticide residue content, and if the problem of excessive pesticide residue content of the foods cannot be found in time, great harm may be caused after people ingest the foods. For another example, currently advocated breast feeding is best feeding for infants only when breast milk has normal nutritional value, but in cases of diseases, medicine taking, surgery or other cases of the mother, the milk secreted by the mother may have reduced content of nutritional elements and even produce viruses, thereby affecting the growth and health of the infants.

However, an existing testing system is generally independent, occupies space, and is inconvenient to store, and a user may forget to use a testing device after the testing device is stored, or does not take out the testing device for use due to bother. For this reason, there exist solutions in the prior art to integrate the testing system for pesticide residue testing on a refrigerator. The existing pesticide residue testing system integrated on the refrigerator tests gas volatilized from the food materials or condensed water flowing down from the food materials, and a gas collection device or a liquid collection device is required to be arranged, such that the structure is quite complex, occupied space is large to affect a normal storage space of the user, and the testing accuracy is quite low, thereby greatly influencing the use experience of the user.

BRIEF DESCRIPTION OF THE INVENTION

An object of the present invention is to overcome at least one of the drawbacks of the prior art and to provide a refrigerator integrating a microfluidic testing system having a simple structure.

A further object of the present invention is to improve the operation convenience of replacement of a microfluidic biochip by a user.

Another object of the present invention is to dampen vibrations, reduce operational noises, and improve the heat dissipation efficiency of the microfluidic testing system.

In order to achieve the above objects, the present invention provides a refrigerator, including a microfluidic testing system used for qualitatively or quantitatively testing a preset test parameter of a sample liquid, the microfluidic testing system including:

a microfluidic biochip which is provided with a sample inlet, a communication port and a testing pool formed inside the microfluidic biochip, wherein the sample inlet, the testing pool and the communication port are in sequential communication by means of a micro-channel;

a chip mounting mechanism used for mounting the microfluidic biochip;

a sample liquid driving device in hermetic communication with the communication port, so as to promote the sample liquid in contact with the sample inlet to flow into the micro-channel and flow to the testing pool via the micro-channel; and a testing mechanism used for testing the testing pool to obtain the preset test parameter of the sample liquid.

Optionally, the sample liquid driving device forms a fluid-tight connection with the communication port through a sealed docking mechanism; and the communication port of the microfluidic biochip is fixedly provided with a plug pin protruding and extending outward, an internal flow channel of the plug pin is in sealed communication with the communication port, the plug pin is inserted into the inside of the sealed docking mechanism and forms a fluid-tight connection with the sealed docking mechanism, and the sealed docking mechanism is in fluid-tight connection with the sample liquid driving device, so that the sample liquid driving device is in sealed communication with the communication port.

Optionally, an end surface of an extended tip of the plug pin is a continuous and smooth hemispherical surface, and a pin hole of the plug pin for fluid communication with the sealed docking mechanism is formed on the circumferential side of a section of the plug pin located inside the sealed docking mechanism.

Optionally, the microfluidic testing system further includes:

a chip withdrawing mechanism used for operably releasing the support effect of the chip mounting mechanism on the microfluidic biochip, so as to release the microfluidic biochip.

Optionally, the chip mounting mechanism includes two oppositely arranged elastic clamping jaws, to apply opposite acting forces to the microfluidic biochip located between the two elastic clamping jaws, such that the microfluidic biochip is clamped between the two elastic clamping jaws; and the chip withdrawing mechanism is configured to operably apply opposite acting forces to the two elastic clamping jaws to make the two elastic clamping jaws elastically deform in directions departing from each other, so as to release the clamping effect of the two elastic clamping jaws on the microfluidic biochip.

Optionally, the microfluidic testing system further includes:

a sample stage for placing a sample cup, the sample cup being used for containing the sample liquid; and the sample stage is configured to be controllably or operatively moved to transport the sample cup placed thereon by the sample stage to a position allowing the sample liquid in the sample cup to be in contact with the sample inlet of the microfluidic biochip.

Optionally, the microfluidic biochip is provided above the sample stage, and the sample inlet is located at the bottom of the microfluidic biochip; and the microfluidic testing system further includes a lifting mechanism for driving the sample stage to move up and down, such that the sample stage is switched between a testing position allowing the sample liquid in the sample cup placed on the sample stage to be in contact with the sample inlet and an initial position at a preset distance below the testing position.

Optionally, the microfluidic testing system further includes:

a buffer liquid bottle used for containing a buffer liquid; and a buffer liquid driving device communicated with the buffer liquid bottle to controllably drive the buffer liquid in the buffer liquid bottle into the sample cup placed on the sample stage, such that the buffer liquid is mixed with a sample in the sample cup to generate the sample liquid.

Optionally, the sample liquid driving device is adjacently provided on the transverse side of the microfluidic biochip, and includes a suspended driving motor.

Optionally, the microfluidic testing system further includes:

a sample stage for placing a sample cup, the sample cup being used for containing the sample liquid; and the sample stage includes a support stage for supporting the sample cup and an oscillator provided at the support stage, and the oscillator is used for oscillating the sample cup after the sample cup is placed on the support stage, such that the buffer liquid and the sample in the sample cup are fully mixed to generate the sample liquid.

Optionally, the microfluidic testing system further includes:

a housing, the chip mounting mechanism, the sample liquid driving device, the testing mechanism, and at least a part of the microfluidic biochip being arranged within the housing; and the housing is provided with a structural connecting piece for being connected with a cabinet or a door of the refrigerator and an electrical connecting piece for forming an electrical connection between the microfluidic testing system and an electrical control device of the refrigerator, so as to allow the microfluidic testing system to be mounted to the cabinet or the door of the refrigerator as a whole.

Optionally, the refrigerator further includes:

the cabinet internally defining a storage space for storing articles; and the door connected to the cabinet and used for opening and/or closing the storage space;

wherein the microfluidic testing device is provided on the door.

The refrigerator according to the present invention includes the microfluidic testing system, and the microfluidic testing system includes the microfluidic biochip for providing testing conditions and testing environments, the chip mounting mechanism for mounting the microfluidic biochip, the sample liquid driving device for accurately controlling the sample liquid to flow into the microfluidic biochip, and the testing mechanism for executing a testing operation. The combination of the structure and the function of the four modules not only can smoothly execute the sample feeding and testing operations, but also can ensure the accuracy of a testing result by means of the accurate control over sample feeding. On this basis, each module has a quite simple structure, thus simplifying the structure of the microfluidic testing system, and preventing the microfluidic testing system from occupying too much space in the refrigerator.

Further, the microfluidic testing system further includes the chip withdrawing mechanism, and a user can release the support effect of the chip mounting mechanism on the microfluidic biochip by operating the chip withdrawing mechanism, such that the microfluidic biochip is released, the user can easily take out the microfluidic biochip or the microfluidic biochip can fall off under the action of the gravity thereof, thus simplifying the operation process of the user, and improving the operation convenience of replacement of the microfluidic biochip by the user.

Further, the sample liquid driving device is provided with the driving motor, and the driving motor is suspended and is not in contact with other structures, which prevents the vibration generated when the driving motor operates from being transmitted to the microfluidic biochip or other structures, thereby dampening the vibration of the whole microfluidic testing system, and reducing the operational noise of the microfluidic testing system. Since the driving motor has a high use frequency and high heat productivity, the suspended arrangement of the driving motor increases the surrounding space thereof to facilitate heat dissipation.

According to the following detailed description of specific embodiments of the present invention in conjunction with drawings, those skilled in the art will better understand the aforementioned and other objects, advantages and features of the present invention.

BRIEF DESCRIPTION OF THE DRAWINGS

Some specific embodiments of the present invention will be described below in detail in an exemplary rather than restrictive manner with reference to the drawings. Identical reference numerals in the drawings represent identical or similar components or parts. Those skilled in the art should understand that these drawings are not necessarily drawn to scale. In the drawings.

DETAILED DESCRIPTION

Figure 1:
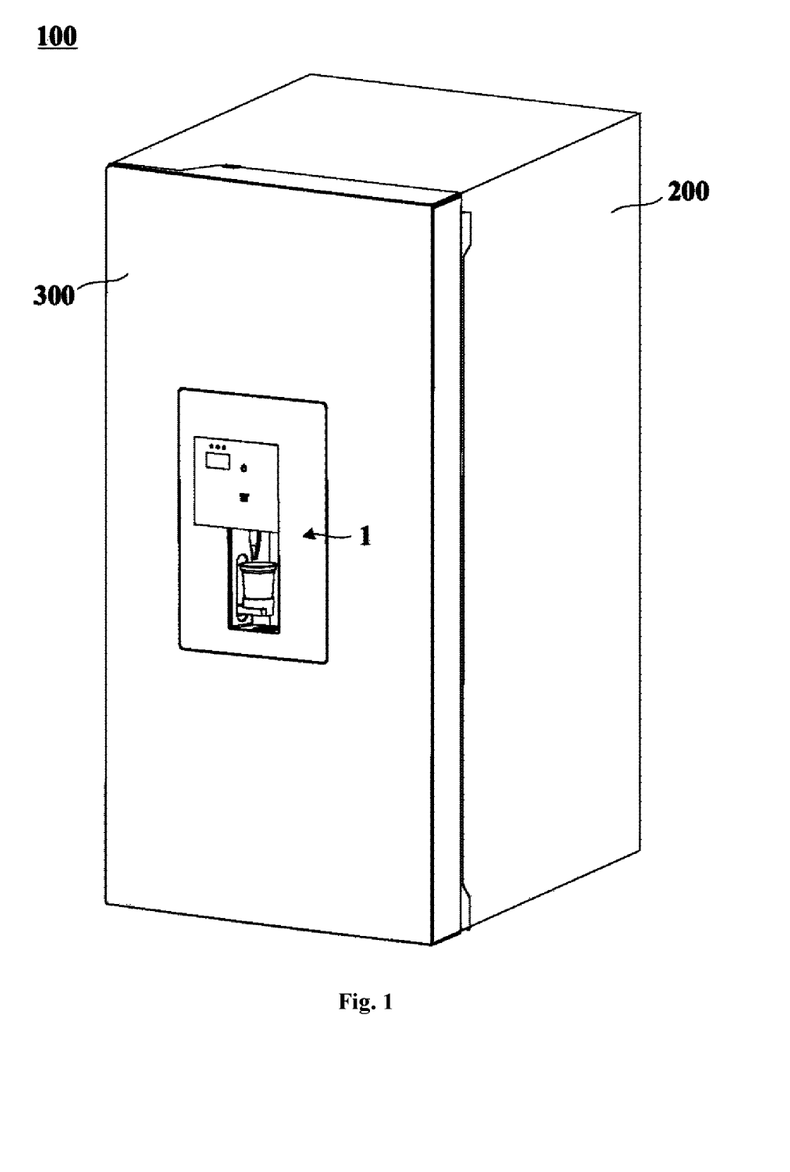
FIG. 1 is a schematic structural diagram of a refrigerator according to an embodiment of the present invention.

The present invention provides a refrigerator. FIG. 1 is a schematic structural diagram of the refrigerator according to an embodiment of the present invention. Referring to FIG. 1, the refrigerator 100 according to the present invention includes a cabinet 200 and a door 300. The cabinet 200 internally defines a storage space for storing articles, and the door 300 is connected to the cabinet 200 and used for opening and/or closing the storage space of the cabinet.

Particularly, the refrigerator 100 further includes a microfluidic testing system 1, the microfluidic testing system 1 is used for qualitatively or quantitatively testing a preset test parameter of a sample liquid; the preset test parameter may be, for example, a pesticide residue parameter for indicating whether a pesticide residue content exceeds the standard and/or a specific value of the pesticide residue content, a nutrient parameter for indicating whether a nutritional element meets the standard and/or a specific content of the nutritional element, a specific substance parameter for indicating whether a specific harmful substance (for example, a specific virus) exceeds the standard and/or a specific content thereof, or the like.

Figure 2:
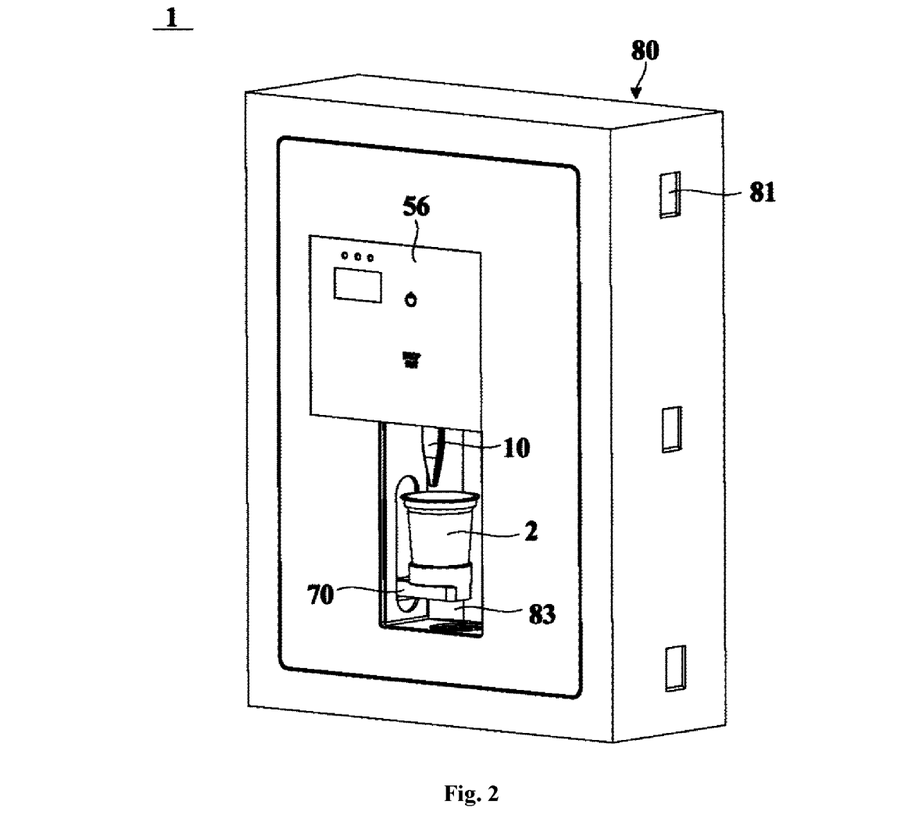
FIG. 2 is a schematic structural diagram of a microfluidic testing system in an embodiment of the present invention.
Figure 3:
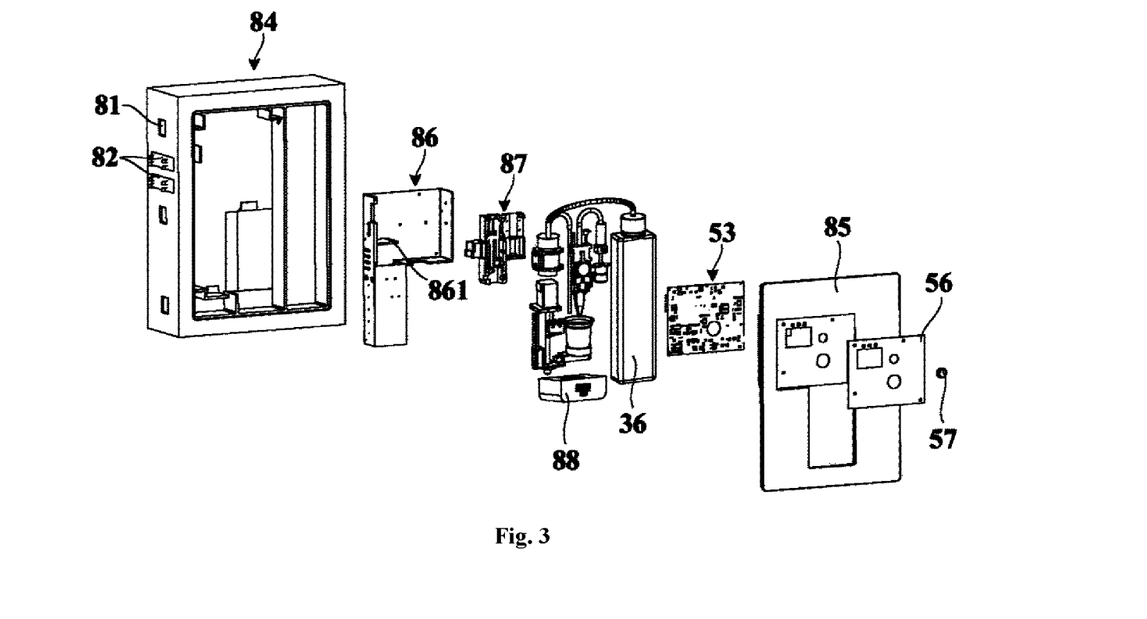
FIG. 3 is a schematic exploded structural diagram of a microfluidic testing system in an embodiment of the present invention.
Figure 4:
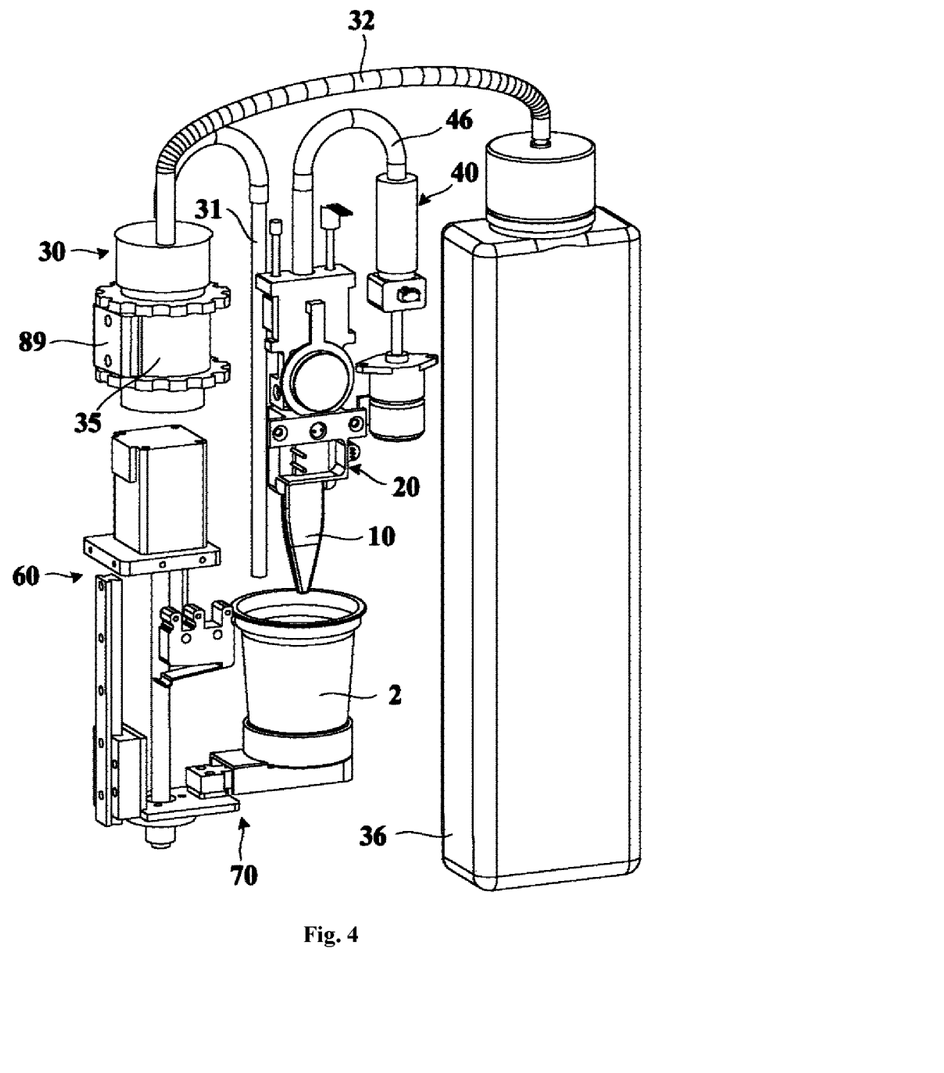
FIG. 4 is a schematic structural diagram of an internal structure of a microfluidic testing system in an embodiment of the present invention.
Figure 5:
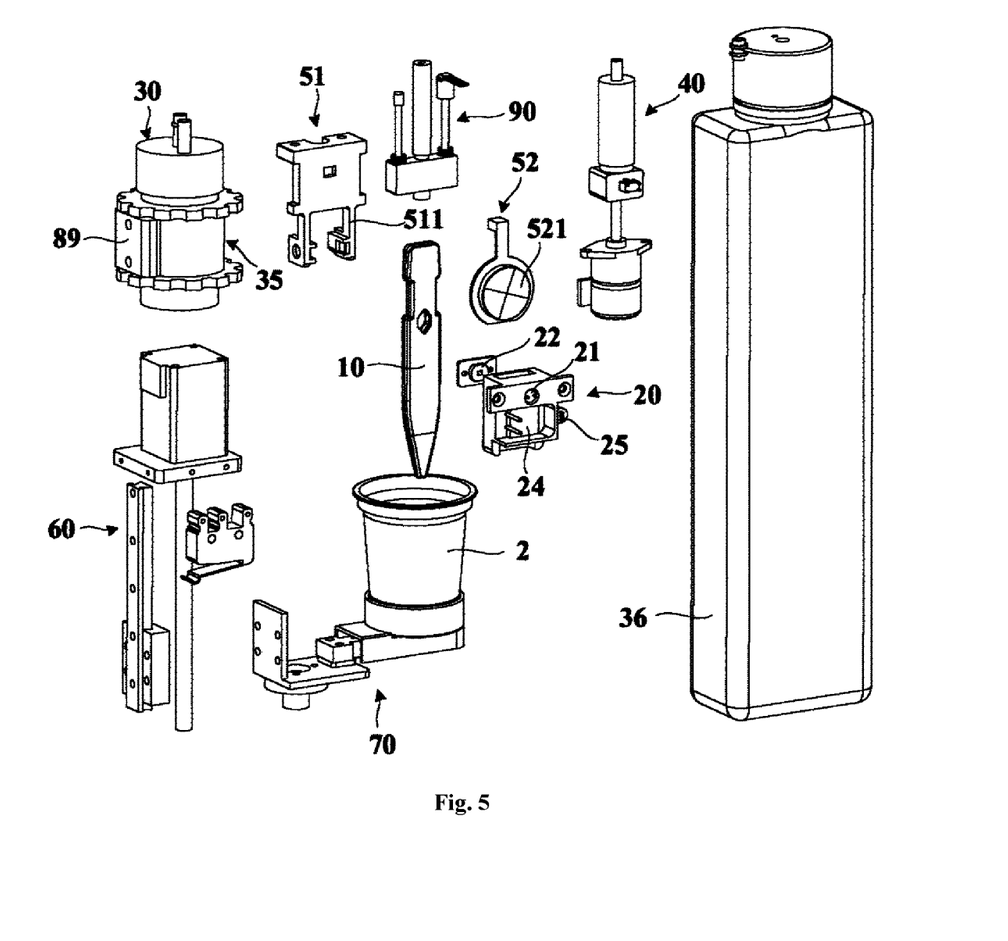
FIG. 5 is a schematic exploded structural diagram of an internal structure of a microfluidic testing system in an embodiment of the present invention.

FIG. 2 is a schematic structural diagram of the microfluidic testing system in an embodiment of the present invention, FIG. 3 is a schematic exploded structural diagram of the microfluidic testing system in an embodiment of the present invention, FIG. 4 is a schematic structural diagram of an internal structure of the microfluidic testing system in an embodiment of the present invention, and FIG. 5 is a schematic exploded structural diagram of the internal structure of the microfluidic testing system in an embodiment of the present invention. For ease of understanding, a sample cup 2 is also shown in FIGS. 1 to 5.

Referring to FIGS. 2 to 5, the microfluidic testing system 1 may include a microfluidic biochip 10, a chip mounting mechanism 51, a sample liquid driving device 40 and a testing mechanism 20. It may be appreciated by those skilled in the art that specific selection of the microfluidic biochip 10 and the testing mechanism 20 used in the microfluidic testing system may vary when the preset test parameters tested by the microfluidic testing system vary. For example, when the microfluidic testing system is used for pesticide residue testing, the microfluidic biochip 10 thereof can be a microfluidic pesticide residue testing chip capable of providing testing conditions for a pesticide residue liquid, and the testing mechanism 20 thereof can be a pesticide residue testing mechanism capable of testing a pesticide residue parameter of the pesticide residue liquid.

Figure 6:
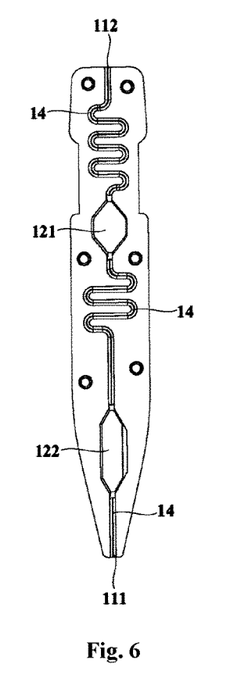
FIG. 6 is a schematic sectional diagram of a microfluidic biochip in an embodiment of the present invention.

FIG. 6 is a schematic sectional diagram of the microfluidic biochip in an embodiment of the present invention; the microfluidic biochip 10 has a sample inlet 111, a communication port 112, and a testing pool 121 formed in the microfluidic biochip, the sample inlet 111, the testing pool 121, and the communication port 112 being communicated in sequence by means of a micro-channel 14 to allow the sample liquid in contact with the sample inlet 111 to enter the micro-channel 14 and flow into the testing pool 121 by means of the micro-channel 14. The micro-channel 14 in the present invention means a micro flow channel or a capillary flow channel having a flow area within a preset size range, so as to have a suitable capability of holding a liquid therein. The sample inlet 111 and the communication port 112 may be formed at an end portion of the microfluidic biochip 10. Further, the sample inlet 111 and the communication port 112 are preferably formed at different end portions of the microfluidic biochip 10.

The chip mounting mechanism 51 is used for mounting the microfluidic biochip 10 to provide supporting for the microfluidic biochip 10.

The sample liquid driving device 40 is in sealed communication with the communication port 112 to promote the sample liquid in contact with the sample inlet 111 to flow into the micro-channel 14 and flow to the testing pool 121 through the micro-channel 14, thereby precisely controlling the quantity and flow rate of the sample liquid entering the testing pool 121.

The testing mechanism 20 is used for testing the testing pool 121, so as to obtain the preset test parameter of the sample liquid. Specifically, the testing pool 121 may be provided therein with a testing reagent in advance, or the testing reagent may be manually or automatically added to the testing pool 121, such that the testing mechanism 20 tests the testing pool 121 after the sample liquid in the testing pool 121 reacts with the testing reagent therein.

The refrigerator 100 according to the present invention includes the microfluidic testing system 1, and the microfluidic testing system 1 includes the microfluidic biochip 10 for providing testing conditions and testing environments, the chip mounting mechanism 51 for mounting the microfluidic biochip 10, the sample liquid driving device 40 for accurately controlling the sample liquid to flow into the microfluidic biochip 10, and the testing mechanism 20 for executing a testing operation. The combination of the structure and the function of the four modules not only can smoothly execute the sample feeding and testing operations, but also can ensure the accuracy of a testing result by means of the accurate control over sample feeding. On this basis, each module has a quite simple structure, thus simplifying the structure of the microfluidic testing system 1, and preventing the microfluidic testing system from occupying too much space in the refrigerator 100.

In a specific embodiment, when the testing mechanism 20 is a pesticide residue testing mechanism for testing the pesticide residue parameters of the pesticide residue liquid, an enzyme inhibition rate method can be used to rapidly and qualitatively test whether pesticide residues in the sample liquid exceed the standard. At this point, the microfluidic biochip 10 further includes a reaction pool 122 formed therein, and the reaction pool 122 is located on a main channel formed by sequentially communicating the sample inlet 111, the testing pool 121, and the communication port 112, and is communicated between the sample inlet 111 and the testing pool 121, such that the sample liquid firstly reacts with a reaction reagent in the reaction pool 122 and then flows into the testing pool 121. The reaction pool 122 is communicated with the sample inlet 111 through the micro-channel 14, and the reaction pool 122 is communicated with the testing pool 121 through the micro-channel 14. The reaction reagent and the testing reagent for pesticide residue testing may be an enzyme reagent and a color developing agent respectively. The reaction pool 122 is configured to allow the sample liquid to react with the enzyme reagent therein, and the sample liquid after the reaction with the enzyme reagent flows into the testing pool 121 to react with the color developing agent in the testing pool 121. The testing mechanism 20 may be selected as a photoelectric testing mechanism and may include a light source 21 and a photosensitive element 22 arranged on two opposite sides of the microfluidic biochip 10 respectively and directly facing the testing pool 121, light emitted from the light source 21 is irradiated to the testing pool 121, and light transmitted through the testing pool 121 is introduced into the photosensitive element 22, which facilitates judgment of the change in an absorbance in the testing pool 121 using a light intensity signal received by the photosensitive element 22, and then facilitates calculation of a pesticide residue inhibition rate. Further, the testing mechanism 20 further includes a heating sheet 24 for supplying heat to the testing pool 121 and a temperature controller 25 for controlling the heating power of the heating sheet 24 to be constant, such that the sample liquid and the testing reagent in the testing pool 121 can react sufficiently and rapidly.

In some embodiments, the sample liquid driving device 40 may be adjacently provided on the transverse side of the microfluidic biochip 10, such that the compactness of the structural layout between the microfluidic biochip 10 and the sample liquid driving device 40 is guaranteed, and a liquid in the microfluidic biochip 10 flows or drops downwards along the microfluidic biochip 10 without contacting the sample liquid driving device 40 when the liquid leaks or is discharged, thereby avoiding the adverse effect on the sample liquid driving device 40.

Further, the sample liquid driving device 40 may include a suspended driving motor 41. That is, the driving motor 41 is connected to a supporting structure only by the top thereof, and is not in contact with other structures, such that the vibration generated during the operation of the driving motor 41 is prevented from being transmitted to the microfluidic biochip 10 or other structures, which not only prevents the adverse effect on the stability or performance of the microfluidic biochip 10 or other structures, but also dampens the vibration of the entire microfluidic testing system 1 and reduces the operational noise thereof. Furthermore, since the driving motor 41 has a high use frequency and high heat productivity, the suspended arrangement of the driving motor 41 increases the surrounding space thereof to facilitate heat dissipation.

Figure 7:
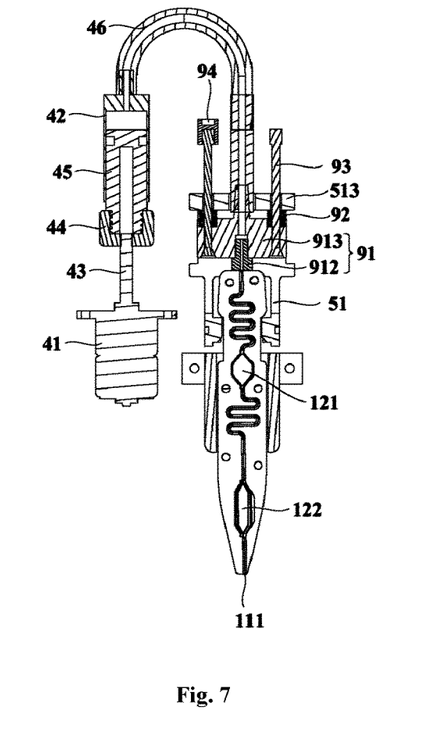
FIG. 7 is a schematic sectional diagram of a sample liquid driving device, a microfluidic biochip and their connection structure in an embodiment of the present invention.

Specifically, the sample liquid driving device 40 may form a negative pressure in the main channel by pumping air outwards, such that the sample liquid in contact with the sample inlet 111 is allowed to enter the main channel under the action of the negative pressure. FIG. 7 is a schematic sectional diagram of the sample liquid driving device, the microfluidic biochip and their connection structure in an embodiment of the present invention. In some embodiments, the sample liquid driving device 40 may be a micro injection pump, and further includes a vertically extending injector 42, a lead screw 43, a slider 44 and a piston 45. The injector 42 is fixed on a bracket 87, and the top of the injector 42 is in sealed communication with the communication port 112 on the top of the microfluidic biochip 10 through a connecting pipeline 46. The lead screw 43 extends vertically and is connected with the driving motor 41 to be rotated under the driving of the driving motor 41. The lead screw 43 penetrates through the slider 44, and the slider is in threaded connection with the lead screw 43 to move up and down along the lead screw 43 with the rotation of the lead screw 43. The piston 45 is provided inside the injector 42 and fixedly connected with the slider 44, so as to be driven by the slider 44 to move in the up-down direction, such that the negative pressure is generated in the main channel when the piston moves downwards, and then, the sample liquid in contact with the sample inlet 111 is impelled to flow into the micro-channel and flow into the testing pool 121 through the micro-channel, and the sample liquid in the main channel is impelled to flow to the sample inlet 111 when the piston moves upwards.

The sample liquid driving device 40 may further include a position sensor, which is used to cooperate with the driving motor 41 to control the amount of displacement of the piston 45 in upward movement and/or downward movement, so as to realize the accurate control over sample feeding. Meanwhile, the amount of displacement of the piston 45 in upward movement and downward movement can be monitored in real time, such that the piston can perform fine pushing and pumping operations, and thus, the sample liquid entering the main channel is subjected to liquid pushing and liquid drawing actions in opposite directions on the premise that the sample liquid is guaranteed not to flow out through the communication port 112, so as to promote more even mixture or a more sufficient reaction between the sample liquid in the testing pool 121 and the testing reagent therein, thus improving the accuracy of the testing result.

In some embodiments, the sample liquid driving device 40 forms a fluid-tight connection with the communication port 112 through a sealed docking mechanism 90. Referring to FIG. 7, the sealed docking mechanism 90 may include a sealed connecting piece 91 and an elastic pressing piece 92. The sealed connecting piece 91 is connected between the microfluidic biochip 10 and the sample liquid driving device 40, and is provided therein with a connection channel penetrating through the sealed connecting piece 91. The elastic pressing piece 92 is used for applying an elastic acting force to the sealed connecting piece 91, such that the sealed connecting piece 91 is simultaneously and hermetically docked with the sample liquid driving device 40 and the microfluidic biochip 10, thereby enabling the sample liquid driving device 40 and the communication port 112 of the microfluidic biochip 10 to be in sealed communication through the connection channel inside the sealed connecting piece 91. Thus, the elastic acting force can be applied to the sealed connecting piece 91 by the elastic pressing piece 92, such that the sealed connecting piece 91 is promoted to be always kept in a state of being tightly and hermetically docked with the sample liquid driving device 40 and the microfluidic biochip 10 at the same time, and the problems of looseness, breakage, or the like, caused by long-time use of other docking mechanisms are avoided, thereby guaranteeing a long-term and reliable fluid-tight communication relationship between the sample liquid driving device 40 and the communication port 112 of the microfluidic biochip 10, and improving the sealing effect therebetween.

In some embodiments, the sample liquid driving device 40 is communicated with the communication port 112 through the connecting pipeline 46. The communication port 112 may be formed on the top of the microfluidic biochip 10, and the sample liquid driving device 40 may be adjacently provided on the transverse side of the microfluidic biochip 10, so as to prevent the sample liquid driving device 40 from being adversely affected by liquid leakage which may be generated by the microfluidic biochip 10. The connecting pipeline 46 may be communicated with the top of the sample liquid driving device 40 to be bridged between the sample liquid driving device 40 and the microfluidic biochip 10.

Further, the sealed connecting piece 91 may include a first connection block 912 for being directly docked with the microfluidic biochip 10 and a second connection block 913 provided on a side of the first connection block 912 away from the microfluidic biochip 10. The first connection block 912 and the second connection block 913 are hermetically connected by means of insertion, and the second connection block 913 and the connecting pipeline 46 are hermetically connected by means of insertion.

In some embodiments, the elastic pressing piece 92 may be a spring, one end of the spring abuts against a fixedly arranged end plate 513, the other end of the spring abuts against the sealed connecting piece 91, and the end plate 513 and the microfluidic biochip 10 are located on two opposite sides of the sealed connecting piece 91 respectively. Specifically, in a mounted state of the microfluidic biochip 10, the spring is in a compressed state to generate the elastic acting force for urging the sealed connecting piece 91 to have a tendency to move towards the microfluidic biochip 10. The number of the elastic pressing pieces 92 may be two or more, so as to increase the elastic acting force acting on the microfluidic biochip 10, and to make the elastic acting force applied to the microfluidic biochip 10 more balanced, thereby avoiding inclination and further improving the sealed connection effect.

Further, the sealed docking mechanism 90 further includes a guide rod 93 sleeved with the spring to prevent the spring from being displaced. One end of the guide rod 93 is fixedly connected with the sealed connecting piece 91, and the other end of the guide rod 93 is in contact with a Hall switch 94 after the microfluidic biochip 10 and the sealed connecting piece 91 are hermetically docked, such that the Hall switch 94 is prompted to generate a trigger signal for indicating that the microfluidic biochip 10 is mounted in place, so as to prompt a user, thus avoiding structural damage caused by excessive mounting of the microfluidic biochip 10, and meanwhile improving the use experience of the user.

Figure 8:
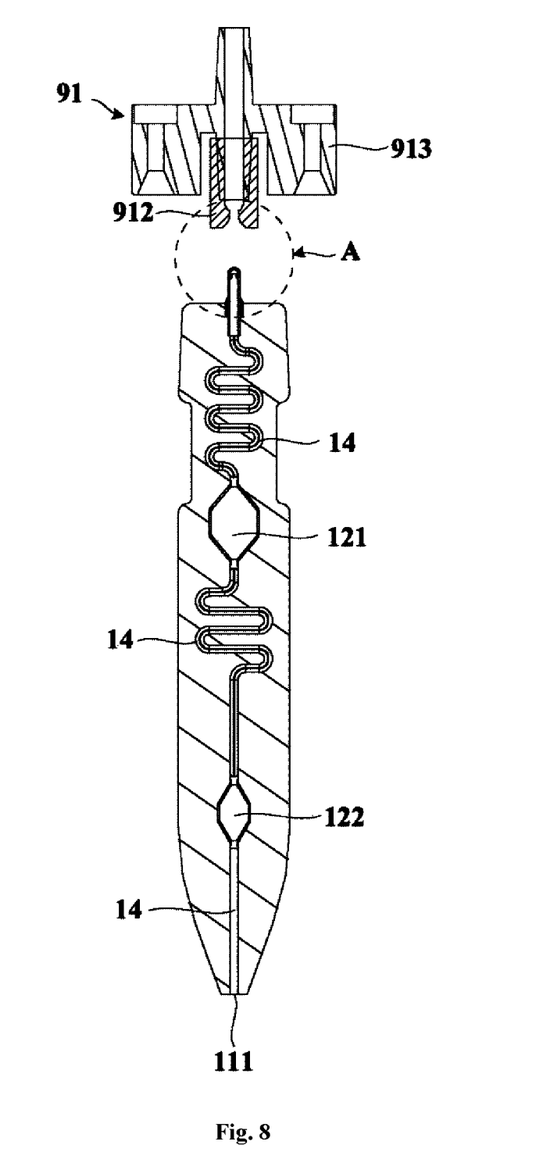
FIG. 8 is a schematic exploded sectional diagram of a sealed docking mechanism and a microfluidic biochip in another embodiment of the present invention.
Figure 9:
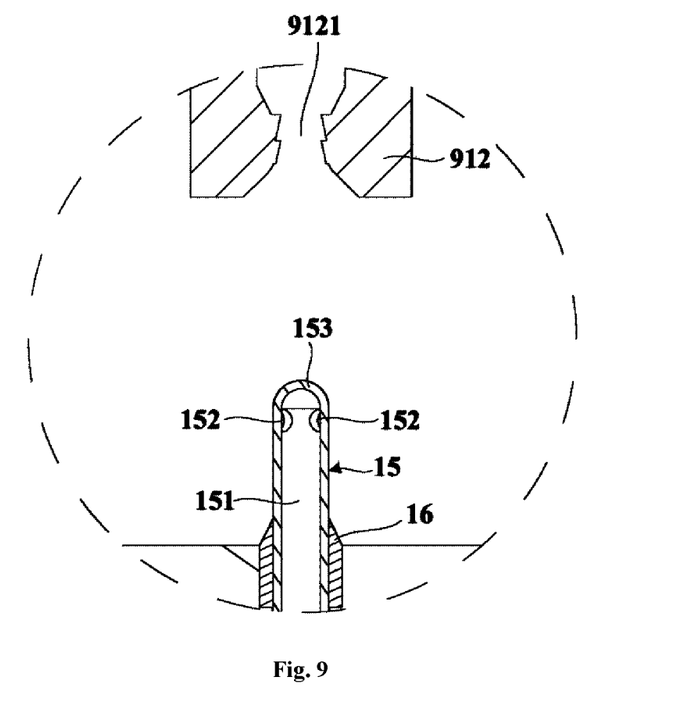
FIG. 9 is a schematic enlarged diagram of part A in FIG. 8.

In order to improve the sealing performance between the sealed docking mechanism 90 and the microfluidic biochip 10, the present application further provides the sealed docking mechanism 90 and the microfluidic biochip 10 according to another embodiment. FIG. 8 is a schematic exploded sectional diagram of the sealed docking mechanism and the microfluidic biochip in another embodiment of the present invention, and FIG. 9 is a schematic enlarged diagram of part A in FIG. 8. In FIG. 8, the elastic pressing piece, the guide rod, or the like, of the sealed docking mechanism are not shown. In some other embodiments, a plug pin 15 protruding and extending outward is fixedly connected to the communication port 112 of the microfluidic biochip 10 in the present invention, an internal flow channel 151 of the plug pin 15 is in sealed communication with the communication port 112, and the plug pin 15 is inserted into the inside of the sealed docking mechanism 90 and forms the fluid-tight connection with the sealed docking mechanism 90. That is, the sealed docking mechanism 90 is simultaneously in fluid-tight connection with the sample liquid driving device 40 and the plug pin 15, thus realizing a good sealed communication relationship between the sample liquid driving device 40 and the communication port 112 of the microfluidic biochip 10.

Specifically, the plug pin 15 can be plugged into the sealed connecting piece 91 of the sealed docking mechanism 90. The sealed connecting piece 91 in the embodiment shown in FIGS. 8 and 9 has a slightly different structure from the sealed connecting piece 91 of the embodiment shown in FIG. 7. The bottom of the first connection block 912 of the sealed connecting piece 91 in the embodiment shown in FIGS. 8 and 9 may be provided with a through hole 9121 for inserting the plug pin 15, and the through hole 9121 and the plug pin 15 may be hermetically matched by means of abutting contact or pressing contact. The plug pin 15 may be provided with a pin hole 152 for fluidly connecting the internal flow channel 151 thereof with the inside of the sealed docking mechanism 90, and the pin hole 152 is formed in a section of the plug pin 15 located inside the sealed docking mechanism 90; that is, the pin hole 152 of the plug pin 15 is located inside the sealed docking mechanism 90, so as to guarantee a smooth and good fluid communication relationship therebetween, improve the sealing performance therebetween to a great extent, and avoid the problems of air leakage, liquid leakage, or the like, at the connection therebetween.

Further, in order to avoid damage to the sealed docking mechanism 90 after frequent insertion and removal of the plug pin 15, the structural strength of the sealed docking mechanism 90 may be increased, which, however, has a higher requirement for a material of the sealed docking mechanism 90, and even if a material having higher structural strength is adopted, the sealed docking mechanism 90 may still be structurally damaged after the plug pin 15 is inserted and removed a limited number of times. For this reason, the applicant of the present application improves the structure of the plug pin 15 from another perspective. Referring to FIG. 9, an end surface 153 of an extended tip of the plug pin 15 is a continuous and smooth hemispherical surface, and the pin hole 152 of the plug pin 15 for fluid communication with the sealed docking mechanism 90 is formed on the circumferential side 154 of the section of the plug pin 15 located inside the sealed docking mechanism 90. Thus, when the microfluidic biochip 10 provided with the plug pin 15 is hermetically docked with the sealed docking mechanism 90, the contact surface between the plug pin 15 and the sealed docking mechanism 90 is a smooth spherical surface, such that friction between the plug pin 15 and the sealed docking mechanism 90 is reduced, the sealed docking mechanism 90 cannot be scratched or punctured, the sealed docking mechanism 90 is guaranteed to keep a good sealed docking function for a long time, the service life of the microfluidic testing system 1 is prolonged, and meanwhile, the requirement for the structural strength of the sealed docking mechanism 90 is reduced.

It should be noted that the extended tip of the plug pin 15 means an end of the plug pin 15 extending into the sealed docking mechanism 90. Further, the pin hole 152 may be formed at the circumferential side of a section of the plug pin 15 close to the extended tip thereof, and thus, the fluid communication relationship between the plug pin 15 and the sealed docking mechanism 90 may be guaranteed even if the section of the plug pin 15 inserted into the sealed docking mechanism 90 is not long.

Still further, referring to FIGS. 8 and 9, the plug pin 15 is inserted into the microfluidic biochip 10 through the communication port 112, and a starting end of the plug pin 15 extending into the microfluidic biochip 10 is open to be communicated with the micro-channel 14, so as to be communicated with the communication port 112. The matching interface between the plug pin 15 and the communication port 112 can be sealed by sealing gum 16 to enhance the sealing performance between the plug pin 15 and the microfluidic biochip 10.

In some alternative embodiments, the plug pin 15 and the microfluidic biochip 10 may also be integrally formed.

In some embodiments, the microfluidic testing system 1 further includes a chip withdrawing mechanism 52 used for operably releasing the support effect of the chip mounting mechanism 51 on the microfluidic biochip 10, so as to release the microfluidic biochip 10. Thus, the user can release the support effect of the chip mounting mechanism 51 on the microfluidic biochip 10 by operating the chip withdrawing mechanism 52, such that the microfluidic biochip 10 is released, the user can easily take out the microfluidic biochip 10 or the microfluidic biochip 10 can fall off under the action of the gravity thereof, thus simplifying an operation process of the user, and improving the operation convenience of replacement of the microfluidic biochip 10 by the user.

Further, the chip withdrawing mechanism 52 may be exposed outside the refrigerator 100 to facilitate the user to carry out a chip withdrawing operation, and no matter how compact the structural layout of the microfluidic testing system 1 itself and the overall structural layout generated after the microfluidic testing system is integrated in the refrigerator are, a detaching operation of the microfluidic biochip 10 is not affected, thereby improving the use experience of the user.

Figure 10:
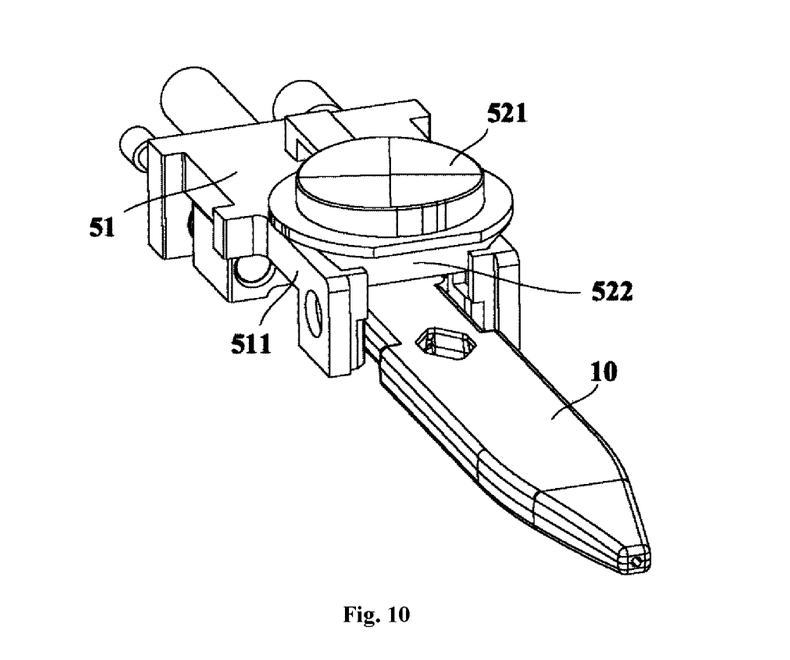
FIG. 10 is a schematic structural diagram of a microfluidic biochip, a chip mounting mechanism, and a chip withdrawing mechanism in an embodiment of the present invention.

FIG. 10 is a schematic structural diagram of the microfluidic biochip, the chip mounting mechanism, and the chip withdrawing mechanism in an embodiment of the present invention. In some embodiments, the chip mounting mechanism 51 may include two oppositely arranged elastic clamping jaws 511, to apply opposite acting forces to the microfluidic biochip 10 located between the two elastic clamping jaws 511, such that the microfluidic biochip 10 is clamped between the two elastic clamping jaws 511. The chip withdrawing mechanism 52 is configured to operably apply opposite acting forces to the two elastic clamping jaws 511 to make the two elastic clamping jaws 511 elastically deform in directions departing from each other, so as to release the clamping effect of the two elastic clamping jaws 511 on the microfluidic biochip 10.

Specifically, the chip withdrawing mechanism 52 may include a cantilever button 521 suspended on one side of the microfluidic biochip 10 and an abutting block 522 protruding and extending towards the microfluidic biochip 10 from the inner side of the cantilever button 521 towards the microfluidic biochip 10, and the abutting block 522 abuts against the oppositely arranged inner sides of the two elastic clamping jaws 511 at the same time, so as to apply outward acting forces to the inner sides of the two elastic clamping jaws 511 by the abutting block 522 when the cantilever button 52 is subjected to an acting force towards the microfluidic biochip 10, such that the two elastic clamping jaws 511 elastically deform towards outer side directions departing from each other. That is, when the microfluidic biochip 10 is required to be disassembled, the user is only required to press the cantilever button 521 to release the clamping effect of the two elastic clamping jaws 511 on the microfluidic biochip 10, so as to release the microfluidic biochip 10, and the operation is quite simple and convenient; the chip withdrawing mechanism 52 has a quite simple structure and a quite ingenious design.

The two opposite side surfaces of the abutting block abutting against the inner sides of the two elastic clamping jaws 511 respectively are oppositely inclined towards the microfluidic biochip 10, so as to guarantee the smoothness of the pressing operation of the cantilever button 521 and avoid the phenomena of blockage, or the like. Specifically, the abutting block may substantially have a shape of an isosceles trapezoid, the lower base of the isosceles trapezoid is connected to the cantilever button 521, and two waists of the isosceles trapezoid abut against the inner sides of the two elastic clamping jaws 511 respectively.

In some embodiments, the microfluidic testing system 1 further includes a sample stage 70, the sample stage 70 is used for placing the sample cup 2, and the sample cup 2 is used for containing the sample liquid. The sample stage 70 is configured to be controllably or operatively moved to transport the sample cup 2 placed thereon by the sample stage 70 to a position allowing the sample liquid in the sample cup 2 to be in contact with the sample inlet 111 of the microfluidic biochip 10. Thus, sample loading of the microfluidic biochip 10 is realized. The user is only required to place the sample cup 2 on the sample stage 70, or after placing the sample cup 2 on the sample stage 70, the user moves the sample stage 70 to a position where the sample liquid is in contact with the sample inlet 111 of the microfluidic biochip 10, such that a sample loading operation is quite convenient, and time and labor are saved. In addition, in the present application, the sample stage 70 is configured to be movable, thus omitting complex structures, such as a sample liquid delivery pump, a delivery pipeline, a sampling needle, or the like, such that the microfluidic testing system 1 has a quite simple structure, and thus is prevented from occupying too much space of the refrigerator.

Further, the microfluidic biochip 10 may be provided above the sample stage 70, and the sample inlet 111 is located at the bottom of the microfluidic biochip 10, which facilitates the sample inlet 111 coming into contact with the sample liquid in the sample cup 2 placed on the sample stage 70. The microfluidic testing system 1 further includes a lifting mechanism 60 for driving the sample stage 70 to move up and down, such that the sample stage 70 is switched between a testing position allowing the sample liquid in the sample cup 2 placed on the sample stage 70 to be in contact with the sample inlet 111 and an initial position at a preset distance below the testing position. That is, the sample stage 70 may be automatically lifted and lowered by the lifting mechanism 60, thus further simplifying the operation of the user, and improving the automation degree of the microfluidic testing system.

Figure 11:
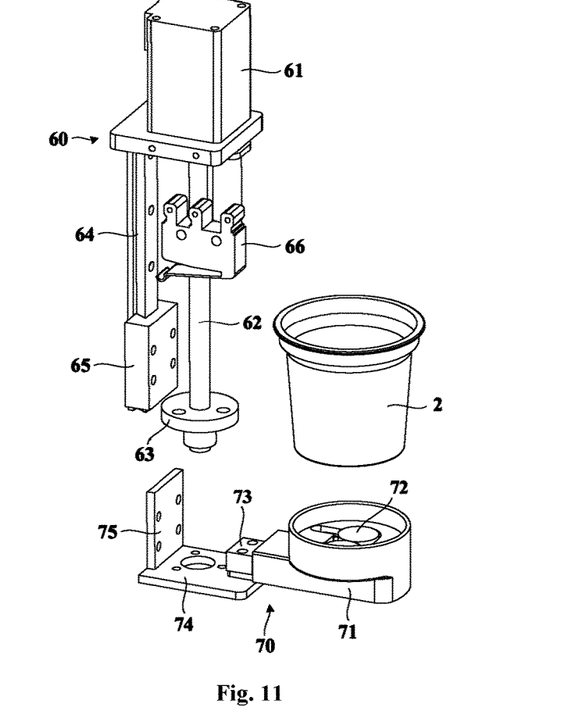
FIG. 11 is a schematic structural diagram of a lifting mechanism and a sample stage in a disassembled state in an embodiment of the present invention.

FIG. 11 is a schematic structural diagram of the lifting mechanism and the sample stage in a disassembled state in an embodiment of the present invention. In some embodiments, the lifting mechanism 60 may include a lifting motor 61, a transmission lead screw 62, and a nut 63. The lifting motor 61 is used to output a driving force. The transmission lead screw 62 is vertically provided and connected with an output shaft of the lifting motor 61 to be rotated under the driving of the lifting motor 61. The transmission lead screw 62 penetrates through the nut 63, and the nut is in threaded connection with the transmission lead screw 62 to move up and down along the transmission lead screw 62 with the rotation of the transmission lead screw 62. The sample stage 70 is fixedly connected with the nut 63 so that the nut 63 drives the sample stage 70 to move up and down.

Further, the lifting mechanism 60 further includes a slide rail 64 and a slider 65. The slide rail 64 is provided beside the transmission lead screw 62 in parallel with the transmission lead screw 62, the slider 65 is movably provided on the slide rail 64, and the sample stage 70 is fixedly connected with the slider 65, and thus the sample stage 70 is guided to move up and down through the cooperation of the slide rail 64 and the slider 65. Specifically, the slider 65 is driven to move synchronously when the sample stage 70 moves in the up-down direction under the action of a driving module, the slider 65 is limited on the slide rail 64, and the slide rail 64 has guiding and limiting effects on the movement of the slider 65, such that the sample stage 70 is indirectly guided and limited, the sample stage 70 is prevented from being shifted or jammed in a moving process, and the movement stability of the sample stage 70 is improved. Specifically, the sample stage 70 may include a horizontal connecting plate 74 through which the transmission lead screw 62 penetrates and which is fixedly connected with the nut 63, and a vertical connecting plate 75 extending upwards perpendicular to the horizontal connecting plate 74, the vertical connecting plate 75 being fixedly connected with the slider 65.

In some embodiments, the lifting mechanism 60 further includes a limit switch 66, and the limit switch 66 is provided close to an upper portion of the transmission lead screw 62 to cause the lifting motor 61 to stop operation when the sample stage 70 moves upwards to touch the limit switch 66. The position of the limit switch 66 is set such that the sample stage 70 is located at the testing position thereof when the lifting motor 61 stops operation under the trigger of the limit switch 66. The sample stage 70 may be kept at the testing position thereof when the lifting motor 61 does not operate. In the present application, the testing position of the sample stage 70 is positioned by the limit switch 66, the positioning is accurate, and the problem that the sample stage 70 exceeds the testing position thereof and continues to move to cause structural damage to the sample stage 70, the microfluidic biochip 10, or the like, can be avoided.

In some embodiments, the sample stage 70 may include a support stage 71 and an oscillator 72. The support stage 71 is used for supporting the sample cup 2. Specifically, the support stage 71 may be a horizontally placed support plate, and a groove for placing the bottom of the sample cup 2 therein may be provided on the support plate, so as to prevent the sample cup 2 from toppling or shaking during the moving process of the sample stage 70, thereby improving the stability of the placement of the sample cup 2. The support stage 71 is fixedly connected with the horizontal connecting plate 74.

The oscillator 72 is provided at the support stage 71, and is used to oscillate the sample cup 2 after the sample cup 2 is placed on the support stage 71, such that a buffer liquid and a sample in the sample cup 2 are fully mixed to generate the sample liquid, thereby fully dissolving a to-be-tested substance on the sample into the buffer liquid to obtain the sample liquid with a suitable concentration. The buffer liquid may be pre-loaded into the sample cup 2 by means of manual addition or may be automatically delivered to the sample cup 2 by a driving device after the sample cup 2 is placed on the sample stage 70.

In some embodiments, the sample stage 70 further includes a weighing sensor 73, and the weighing sensor 73 is provided below the support stage 71 for weighing the weight of the sample in the sample cup 2, thereby allowing a buffer liquid driving device 30 to deliver a preset quantity of the buffer liquid matched with the weight of the sample to the sample cup 2. In general, the sample is extracted at will by a home user, for example, a small vegetable leaf is torn off at will, and therefore, in order to guarantee the accuracy of a measurement result, the quantity of the buffer liquid input into the sample cup 2 is required to be matched with the quantity of the sample, so as to generate the sample liquid with a proper concentration. In the present application, the weight of the sample can be automatically and accurately obtained by the weighing sensor 73 provided below the support stage 71, such that the buffer liquid driving device 30 is automatically controlled to input the matched quantity of the buffer liquid into the sample cup 2, thus guaranteeing the accuracy of the measurement result, avoiding various problems of inconvenient use, a complex operation, a large error, or the like, caused by manual weighing of the sample by the user, and further improving the automation degree of the microfluidic testing system and the use experience of the user.

It should be noted that, in some alternative embodiments, the sample stage 70 may be fixed, and the microfluidic pesticide residue testing chip 10 may be configured to be movable, which can also facilitate the sampling operation.

In some embodiments, the microfluidic testing system 1 further includes a buffer liquid bottle 36 and the buffer liquid driving device 30. The buffer liquid bottle 36 is used for containing the buffer liquid. The buffer liquid driving device 30 is communicated with the buffer liquid bottle 36 to controllably drive the buffer liquid in the buffer liquid bottle 36 into the sample cup 2 placed on the sample stage 70, such that the buffer liquid is mixed with the sample in the sample cup 2 to generate the sample liquid. Specifically, the buffer liquid bottle 36 is communicated with the buffer liquid driving device 30 through an inlet pipe 32. An outlet pipe 31 of the buffer liquid driving device 30 extends to the sample stage 70. This arrangement is adopted mainly for a solid sample as a tested sample, and the buffer liquid is required to dissolve the to-be-tested substance on the solid sample to form the sample liquid; or, the sample is a liquid sample, but has a too high concentration, and the sample is required to be diluted using the buffer liquid to produce the sample liquid. For example, during pesticide residue testing, the tested sample is usually a solid food residue piece, such as a skin, a leaf, or the like, the sample is required to be placed in the buffer liquid, and the pesticide residue on the sample is dissolved in the buffer liquid to form the sample liquid.

Specifically, the buffer liquid driving device 30 may be a peristaltic pump, a diaphragm pump or other suitable types of driving devices. The peristaltic or diaphragm pump generates large vibrations in the radial direction thereof when in operation, and in order to prevent the vibrations from being transmitted to the microfluidic biochip 10, an elastic damping piece 35 may be provided on the radial outer side of the peristaltic or diaphragm pump. The elastic damping piece 35 may be fitted over the buffer liquid driving device 30 and supported in a housing 80 by the clamping effect of the bracket 87 and a fixed block 89, and the fixed block 89 may be fixed on a support plate 86.

In some embodiments, the microfluidic testing system 1 further includes the housing 80, the chip mounting mechanism 51, the sample liquid driving device 40, the testing mechanism 20, and at least a part of the microfluidic biochip 10 being arranged within the housing 80. The housing 80 is provided with a first structural connecting piece 81 for being connected with the cabinet or the door of the refrigerator 100, and a first electrical connecting piece 82 for forming an electrical connection between the microfluidic testing system 1 and an electrical control device of the refrigerator 100, so as to allow the microfluidic testing system 1 to be mounted to the cabinet or the door of the refrigerator 100 as a whole.

Further, the housing 80 is provided with an operation stage 83 opened towards the front side thereof, and the sample stage 70 is at least partially located in the operation stage 83 to facilitate the user to perform operations of placing the sample cup 2, taking out the sample cup 2, or the like, in the operation stage 83. A water disposal pan 88 located below the sample stage 70 may be provided in the operation stage 83 to receive a possibly dripping liquid, thereby preventing contamination of the operation stage 83.

In some embodiments, the microfluidic testing system 1 further includes a circuit board 53, a display device 56, and a switch button 57, and the circuit board 53 is provided within the housing 80 and electrically connected with the first electrical connecting piece 82 on the housing 80. The electrical components of the microfluidic testing system 1 (for example, the lifting mechanism 60, the buffer liquid driving device 30, the sample liquid driving device 40, the testing mechanism 20, the display device 56, the switch button 57, or the like) are all electrically connected to the circuit board 53 directly or indirectly. The display device 56 is provided on the front side of the housing 80 and electrically connected to the circuit board 53 for displaying the testing result of the testing mechanism 20. The switch button 57 is provided on the front side of the housing 80 and electrically connected to the circuit board 53 for activating and/or deactivating the testing function of the microfluidic testing system 1. That is, the user can start, pause, or stop the testing function of the microfluidic testing system 1 by operating the switch button 57.

In some embodiments, the housing 80 may include a rear shell 84 at the rear side and a front panel 85 connected to the front side of the rear shell 84. An accommodating cavity is defined between the rear shell 84 and the front panel 85 after the rear shell and the front panel are assembled. The support plate 86 and the bracket 87 are further provided in the accommodating cavity of the housing 80. The support plate 86 is fixedly connected to the rear shell 84, and at least a part of the structure of the lifting mechanism 60 (for example, the non-movable part of the lifting mechanism) and the buffer liquid driving device 30 are fixed on the support plate 86. The bracket 87 is fixedly connected to the front side of the support plate 86, and the microfluidic biochip 10 and the sample liquid driving device 40 are directly or indirectly supported on the bracket 87. Thus, the lifting mechanism 60, the buffer liquid driving device 30, the microfluidic biochip 10, and the sample liquid driving device 40 can be stably supported by the support plate 86 and the bracket 87 in the accommodating cavity formed between the rear shell 84 and the front panel 85.

In some embodiments, the lifting mechanism 60 may be provided on the transverse side of the sample stage 70, the buffer liquid driving device 30 may be provided on one side of the microfluidic biochip 10 in the transverse direction and located above the lifting mechanism 60, the sample liquid driving device 40 is located on the other side of the microfluidic biochip 10 in the transverse direction, and the buffer liquid bottle 36 is located on a side of the sample liquid driving device 40 away from the microfluidic biochip 10. For the microfluidic biochip 10, the sample stage 70, the lifting mechanism 60, the buffer liquid driving device 30, the sample liquid driving device 40 and the buffer liquid bottle 36 with such a layout, the size features of each module in the vertical direction and the transverse direction are fully utilized, such that the layout of the modules is more compact, and the occupied space is reduced as much as possible. Moreover, the modules are only arranged side by side in the vertical direction and the transverse direction, such that the thickness of the microfluidic testing system 1 in the front and rear direction is reduced as much as possible, and the microfluidic testing system is more suitable for being integrated on the refrigerator.

Further, a partition 861 extending transversely may be provided between the buffer liquid driving device 30 and the lifting mechanism 60 to avoid that a leaked liquid possibly generated by the buffer liquid driving device 30 drops on the lifting mechanism 60 to affect the normal operation of the lifting mechanism 60. The partition 861 may be fixed on the support plate 86.

In some embodiments, the microfluidic testing device 1 is provided on the door 300, such that the operation is convenient, the original storage space in the cabinet 200 cannot be occupied, and the storage capacity of the refrigerator 100 cannot be influenced.

Figure 12:
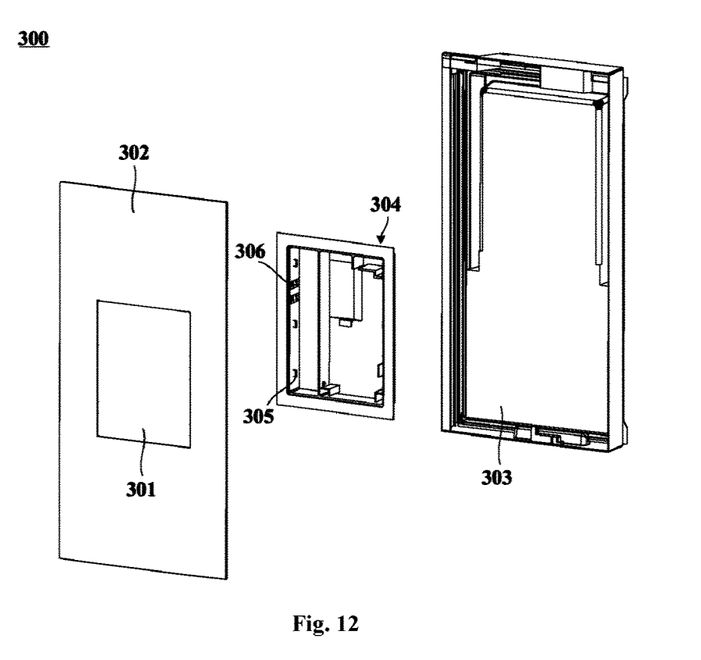
FIG. 12 is a schematic exploded structural diagram of a door in an embodiment of the present invention.

FIG. 12 is a schematic exploded structural diagram of the door in an embodiment of the present invention. In some embodiments, a hollowed window 301 is provided on the front side of the door 300, and the sample stage 70 of the microfluidic testing system 1 is exposed on the front side of the door 300 through the hollowed window 301, such that the user can be allowed to place the sample cup on the sample stage 70 without opening the door 300, thus avoiding the problem that cold leakage is serious due to the door 300 being required to be opened during each test, guaranteeing the heat preservation performance of the refrigerator 100, and saving energy consumption.

Specifically, the door 300 may include a panel 302 for forming a front portion thereof, a door liner 303 for forming a rear portion thereof, and a foamed heat insulation layer (not shown) provided between the panel 302 and the door liner 303, and the hollowed window 301 is formed in the panel 302. A pre-embedded box 304 is pre-embedded between the panel 302 and the door liner 303 before the foamed heat insulation layer is formed, and the microfluidic testing system 1 is provided in the pre-embedded box 304. That is, the pre-embedded box 304 is pre-provided between the panel 302 and the door liner 303 before the door 300 is foamed, so as to reserve a space for mounting the microfluidic testing system 1 between the panel 302 and the door liner 303.

Further, the pre-embedded box 304 is attached to a rear surface of the panel 302, and the front side of the pre-embedded box 304 is open and directly faces the hollowed window 301, such that the microfluidic testing system 1 is allowed to be mounted in the pre-embedded box 304 from front to back through the hollowed window 301, thus improving the mounting convenience of the microfluidic testing system 1.

Specifically, the pre-embedded box 304 can be provided with a second structural connecting piece 305 matched and connected with the first structural connecting piece 81 and a second electrical connecting piece 306 electrically connected with the first electrical connecting piece 82, and the second electrical connecting piece 306 is electrically connected with the electrical control device of the refrigerator 100. Thus, the microfluidic testing system 1 is mounted on the door 300 as a whole by arranging the corresponding structural connecting pieces and electrical connecting pieces on the pre-embedded box 304 and the housing 80, such that the whole microfluidic testing system 1 is connected with the refrigerator 100 in terms of both structure and circuit. Thus, an assembly process of the microfluidic testing system 1 is simplified, and the disassembly or maintenance of the microfluidic testing system 1 is facilitated.

The refrigerator 100 according to the present application is a refrigerator in a broad sense, and includes not only a so-called refrigerator in a narrow sense, but also a storage device having a refrigerating, freezing or other storage function, for example, a refrigerating box, a freezer, or the like.

It should also be understood by those skilled in the art that the terms "up", "down", "front", "rear", "top", "bottom", or the like, used in the embodiments of the present invention are used as terms for indicating the orientation or the positional relationship with respect to the actual use state of the refrigerator 100, and these terms are only used for convenience of description and understanding of the technical solution of the present invention, and do not indicate or imply that the device or the component referred to must have a specific orientation, or be configured and operated in a specific orientation, and therefore, should not be construed as limiting the present invention.

So far, those skilled in the art should be aware that, although plural exemplary embodiments of the present invention have been shown and described herein in detail, a lot of other variations or modifications conforming to the principle of the present invention can still be directly determined or derived from the contents disclosed in the present invention without departing from the spirit and scope of the present invention. Therefore, the scope of the present invention should be understood and deemed as covering all of these other variations or modifications.

What is claimed is:

1. A refrigerator, comprising a microfluidic testing system used for qualitatively or quantitatively testing a preset test parameter of a sample liquid, the microfluidic testing system comprising:
a microfluidic biochip which is provided with a sample inlet, a communication port and a testing pool formed inside the microfluidic biochip, wherein the sample inlet, the testing pool and the communication port are in sequential communication by means of a micro-channel;
a chip mounting mechanism used for mounting the microfluidic biochip;
a sample liquid driving device in hermetic communication with the communication port, so as to promote the sample liquid in contact with the sample inlet to flow into the micro-channel and flow to the testing pool via the micro-channel;
a testing mechanism used for testing the testing pool to obtain the preset test parameter of the sample liquid;
a cabinet internally defining a storage space for storing articles; and
a door connected to the cabinet and used for opening and/or closing the storage space; and
wherein a microfluidic testing device is provided on the door.

2. The refrigerator according to claim 1,
wherein the sample liquid driving device forms a fluid-tight connection with the communication port through a sealed docking mechanism; and
the communication port of the microfluidic biochip is fixedly provided with a plug pin protruding and extending outward, an internal flow channel of the plug pin is in sealed communication with the communication port, the plug pin is inserted into the inside of the sealed docking mechanism and forms a fluid-tight connection with the sealed docking mechanism, and the sealed docking mechanism is in fluid-tight connection with the sample liquid driving device, so that the sample liquid driving device is in sealed communication with the communication port.

3. The refrigerator according to claim 2,
wherein an end surface of an extended tip of the plug pin is a continuous and smooth hemispherical surface, and a pin hole of the plug pin for fluid communication with the sealed docking mechanism is formed on a circumferential side of a section of the plug pin located inside the sealed docking mechanism.

4. The refrigerator according to claim 1, wherein the microfluidic testing system further comprises:
a chip withdrawing mechanism used for operably releasing a support effect of the chip mounting mechanism on the microfluidic biochip, so as to release the microfluidic biochip.

5. The refrigerator according to claim 4,
wherein the chip mounting mechanism comprises two oppositely arranged elastic clamping jaws, to apply opposite acting forces to the microfluidic biochip located between the two elastic clamping jaws, such that the microfluidic biochip is clamped between the two elastic clamping jaws; and
the chip withdrawing mechanism is configured to operably apply opposite acting forces to the two elastic clamping jaws to make the two elastic clamping jaws elastically deform in directions departing from each other, so as to release a clamping effect of the two elastic clamping jaws on the microfluidic biochip.

6. The refrigerator according to claim 1, wherein the microfluidic testing system further comprises:
a sample stage for placing a sample cup, the sample cup being used for containing the sample liquid; and
the sample stage is configured to be controllably or operatively moved to transport the sample cup placed thereon by the sample stage to a position allowing the sample liquid in the sample cup to be in contact with the sample inlet of the microfluidic biochip.

7. The refrigerator according to claim 6,
wherein the microfluidic biochip is provided above the sample stage, and the sample inlet is located at the bottom of the microfluidic biochip; and
the microfluidic testing system further comprises a lifting mechanism for driving the sample stage to move up and down, such that the sample stage is switched between a testing position allowing the sample liquid in the sample cup placed on the sample stage to be in contact with the sample inlet and an initial position at a preset distance below the testing position.

8. The refrigerator according to claim 6, wherein the microfluidic testing system further comprises:
a buffer liquid bottle used for containing a buffer liquid; and
a buffer liquid driving device communicated with the buffer liquid bottle to controllably drive the buffer liquid in the buffer liquid bottle into the sample cup placed on the sample stage, such that the buffer liquid is mixed with a sample in the sample cup to generate the sample liquid.

9. The refrigerator according to claim 1,
wherein the sample liquid driving device is adjacently provided on the transverse side of the microfluidic biochip, and comprises a suspended driving motor.

10. The refrigerator according to claim 1, wherein the microfluidic testing system further comprises:
a sample stage for placing a sample cup, the sample cup being used for containing the sample liquid; and
the sample stage comprises a support stage for supporting the sample cup and an oscillator provided at the support stage, and the oscillator is used for oscillating the sample cup after the sample cup is placed on the support stage, such that a buffer liquid and a sample in the sample cup are fully mixed to generate the sample liquid.

11. The refrigerator according to claim 1, wherein the microfluidic testing system further comprises:
a housing, the chip mounting mechanism, the sample liquid driving device, the testing mechanism, and at least a part of the microfluidic biochip being arranged within the housing; and
the housing is provided with a structural connecting piece for being connected with a cabinet or a door or the refrigerator and an electrical connecting piece for forming an electrical connection between the microfluidic testing system and an electrical control device of the refrigerator, so as to allow the microfluidic testing system to be mounted to the cabinet or the door of the refrigerator as a whole.

* * * * *

UNITED STATES PATENT AND TRADEMARK OFFICE
CERTIFICATE OF CORRECTION

| | | |
|---|---|---|
| PATENT NO. | : 11,883,819 B2 | Page 1 of 1 |
| APPLICATION NO. | : 18/246486 | |
| DATED | : January 30, 2024 | |
| INVENTOR(S) | : Xiaobing Zhu et al. | |

It is certified that error appears in the above-identified patent and that said Letters Patent is hereby corrected as shown below:

In the Claims

In Column 18, Line 58, Claim 11, delete "door or the" and insert -- door of the --, therefor.

Signed and Sealed this
Thirtieth Day of April, 2024

Katherine Kelly Vidal
*Director of the United States Patent and Trademark Office*